United States Patent [19]

Cummins

[11] Patent Number: 5,758,647
[45] Date of Patent: Jun. 2, 1998

[54] SUPPORT AND INDEXING APPARATUS FOR LUMBAR REGION IMAGING

[76] Inventor: Jimmie E. Cummins, 3520 Bocage Dr. — #711, Orlando, Fla. 32812

[21] Appl. No.: 731,641

[22] Filed: Oct. 17, 1996

[51] Int. Cl.⁶ ..................................... A61B 6/00
[52] U.S. Cl. .................. 128/653.5; 5/601; 5/621; 378/180; 378/208
[58] Field of Search .............. 128/653.1, 653.2, 128/653.5, 781, 782; 5/601, 610, 607, 608, 621; 324/318; 378/208, 180

[56] References Cited

U.S. PATENT DOCUMENTS

| | | | |
|---|---|---|---|
| 4,669,106 | 5/1987 | Ammerman | 378/208 |
| 4,834,112 | 5/1989 | Machek et al. | 128/777 |
| 4,923,187 | 5/1990 | Mombrinie | 269/328 |
| 5,197,474 | 3/1993 | Englund et al. | 128/653.5 |
| 5,197,975 | 3/1993 | Mombrinie | 606/238 |
| 5,239,716 | 8/1993 | Fisk | 5/630 |
| 5,243,639 | 9/1993 | Johnson | 378/180 |
| 5,329,924 | 7/1994 | Bonutti | 128/653.1 |
| 5,445,152 | 8/1995 | Bell et al. | 128/653.5 |
| 5,542,423 | 8/1996 | Bonutti | 128/653.1 |
| 5,562,094 | 10/1996 | Bonutti | 128/653.1 |
| 5,577,503 | 11/1996 | Bonutti | 128/653.2 |
| 5,632,275 | 5/1997 | Browne et al. | 128/653.1 |
| 5,640,958 | 6/1997 | Bonutti | 128/653.2 |
| 5,662,122 | 9/1997 | Evans | 128/781 |

*Primary Examiner*—Marvin M. Lateef
*Assistant Examiner*—Eleni Mantis Mercader
*Attorney, Agent, or Firm*—Allen, Dyer, Doppelt, Milbrath & Gilchrist, P.A.

[57] ABSTRACT

A support and indexing apparatus and method are provided for use in imaging a lumbar region of a patient. A base is adapted for insertion into a magnetic resonance imaging apparatus, and a support structure is rotatably affixed thereto at a pivot point atop the base. The support structure is adapted for receiving a side of a trunk of the patient, and the pivot point is positioned to permit flexion of the lumbar region. Biasing means are provided for preferentially positioning the support structure in one of a sequential series of rotational positions relative to the base. An indexing mechanism provides an angular measurement of the rotational position.

5 Claims, 4 Drawing Sheets

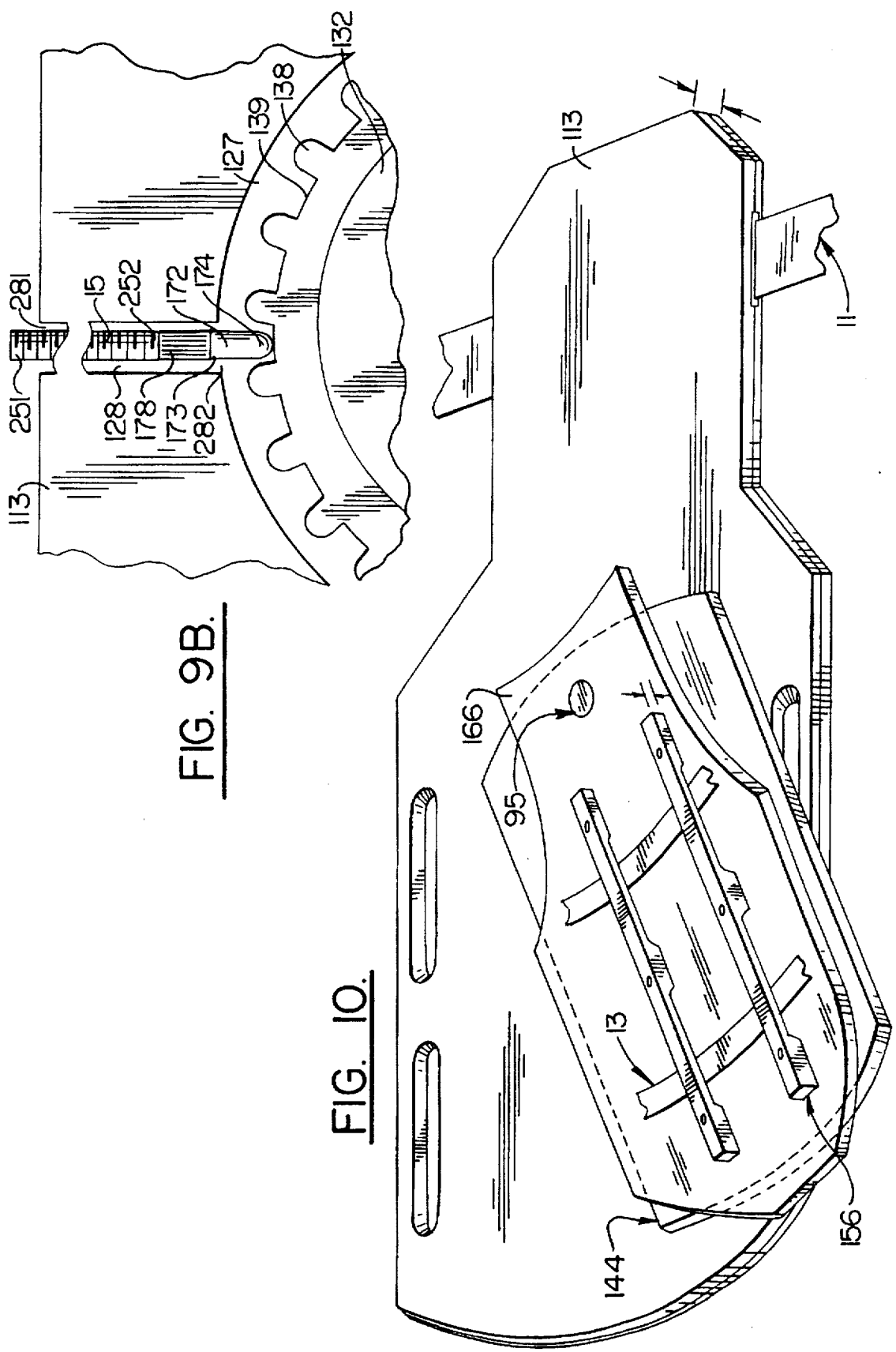

SUPPORT AND INDEXING APPARATUS FOR LUMBAR REGION IMAGING

BACKGROUND OF THE INVENTION

1. Field of the Invention

The present invention relates to devices for use in magnetic resonance imaging, and, more particularly, to support and indexing devices for the study of joints by magnetic resonance imaging.

2. Description of Related Art

Magnetic resonance imaging is known for use to image parts of the body, such as joints. While previously used imaging devices required several minutes to produce an image, state-of-the-art machines permit essentially "real-time" imaging of joints. It is desirable to be able to image joints throughout their natural range of motion, thereby facilitating a diagnosis of any joint problem. It is also desirable to be able to perform such imaging studies reproducibly.

An indexing apparatus for imaging the shoulder joint has been disclosed by Bonutti (U.S. Pat. No. 5,343,580) that is lockable in any selected one of a plurality of sequential index positions.

SUMMARY OF THE INVENTION

It is therefore an object of the present invention to provide an apparatus and method for reproducibly imaging a lumbar region of a patient.

It is another object to provide such an apparatus and method for obtaining a kinematic series of images of the lumbar region of the patient.

It is a further object to provide such an apparatus and method for indexing the movement of the lumbar region of the patient during magnetic resonance imaging.

It is an additional object to provide an apparatus and method for imaging the lumbar region of a patient that permits the patient to move through a natural range of motion unassisted.

These and other objects are achieved by the lumbar support and indexing apparatus and method of the present invention. The apparatus comprises a base that is adapted for insertion into a magnetic resonance imaging apparatus such as one of the types of coils currently in use, although the use with such a coil is not intended as a limitation.

The apparatus further comprises a support structure that is rotatably affixed at a pivot point atop the base. The support structure is adapted for receiving a side of a trunk of the patient; that is, the structure permits the patient to lie on his side, with his shoulder and trunk thereon. The pivot point is positioned to permit flexion and extension of the lumbar region.

Biasing means are provided for preferentially positioning the support structure in one of a sequential series of rotational positions relative to the base. Index means are also provided for permitting the user to obtain an angular measurement of the rotational position. Thus the amount of flexion and extension can be determined and reproduced exactly.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 9B illustrates the gear/marshmallow spring mechanism in the second position.

FIG. 10 is a perspective illustration of the assembled lumbar support device in the second position.

DETAILED DESCRIPTION OF THE PREFERRED EMBODIMENTS

A description of the preferred embodiments of the present invention will now be presented with reference to FIGS. 1–10. Unless stated otherwise, all materials insertable into the imaging device are preferably impervious to magnetic fields, thereby permitting their use in a magnetic resonance imaging device without interfering therewith. An exemplary material comprises a high-density polyethylene such as Sanalite™, a marine-tough polymer (Compression Polymer, Scranton, Pa.).

Figure 1:
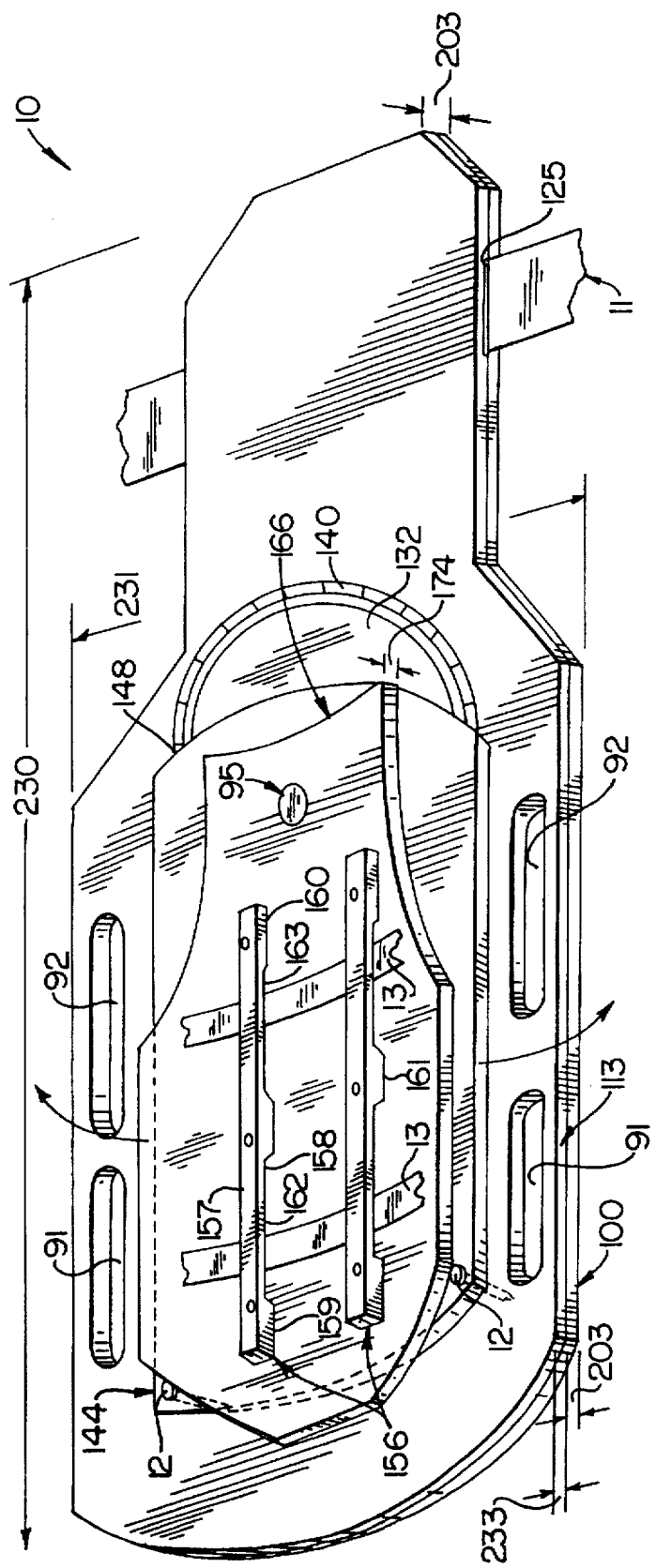
FIG. 1 is a perspective illustration of the assembled lumbar support device in the first position.
Figure 2:
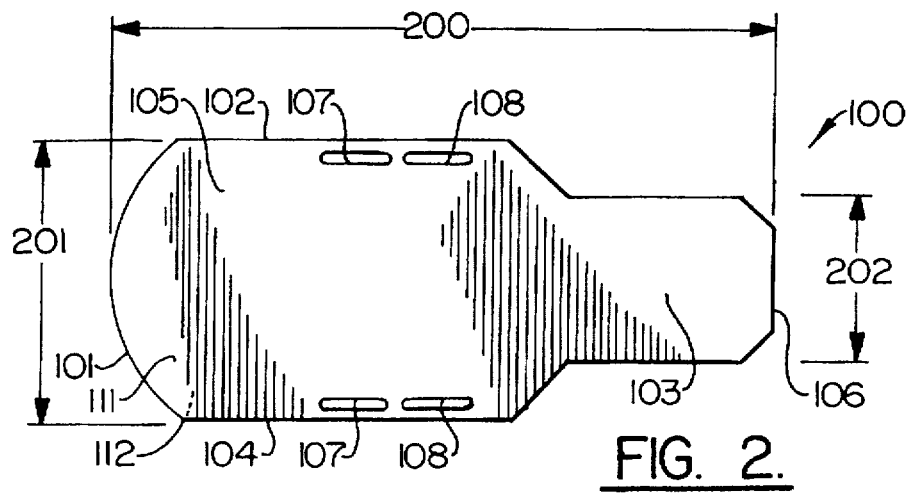
FIG. 2 is a top plan view of the base plate.
Figure 3:
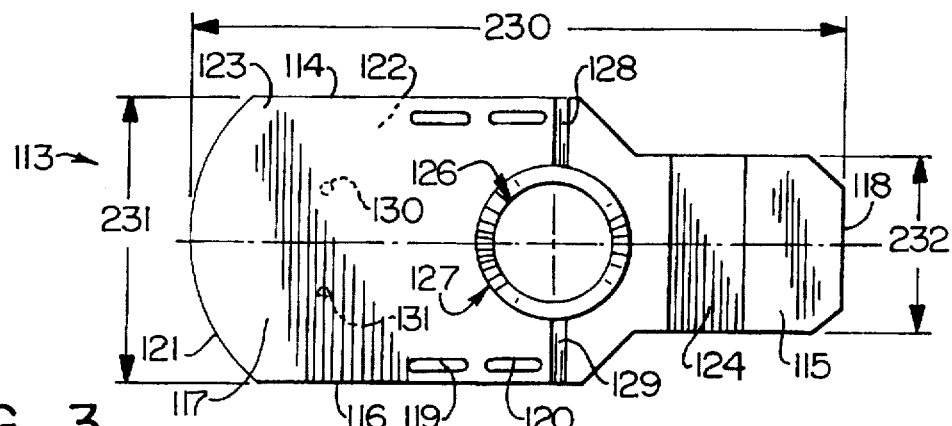
FIG. 3 is a bottom plan view of the top plate.
Figure 4:
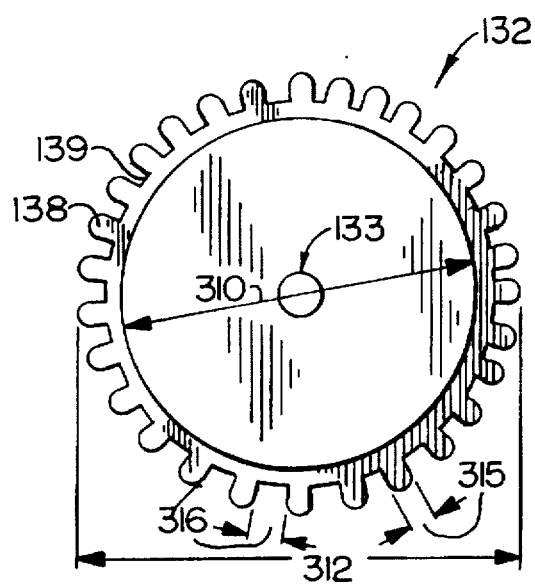
FIG. 4 is a top plan view of the gear.
Figure 5:
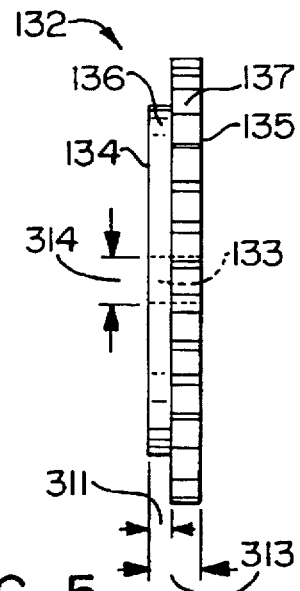
FIG. 5 is a side view of the gear.

The lumbar support device 10 of the present invention, shown assembled in FIG. 1, comprises a generally flat base plate 100 (FIG. 2). Base plate 100 has an outwardly curving first edge 101 meeting two opposing side edges 102,104. The two side edges 102,104 are generally parallel along wider portion 105. Side edges 102,104 then angle inward, again become parallel along a narrower portion 103, and meet second edge 106 with a bevel. In use the head of the patient is placed adjacent the first edge 101.

Base plate 100 further has two pairs of elongated handle slots 107,108 extending from the top face 111 through to the bottom face 112, one pair of slots 107,108 generally adjacent each side edge 102,104 for carrying. In an alternative embodiment, there is one slot adjacent each side edge.

In a preferred embodiment, base plate 100 has a length 200 of 39.25 in., a width 201 along wider portion 105 of 16.5 in., a width 202 along narrower portion 103 of 11.75 in., and a depth 203 of 0.25 in. These dimensions are not intended to be limiting, but will be seen to be representative of dimensions suitable for use in a typical imaging apparatus.

Lumbar support device 10 further comprises a generally flat top plate 113 (FIG. 3) having an outline in plan view generally identical to that of the base plate 100 so that they may be placed one atop the other as shown in FIG. 1. Again, top plate 113 has an outwardly curving first edge 121 meeting two opposing side edges 114,116. The two side edges 114,116 are generally parallel along wider portion 117. Side edges 114,116 then angle inward, again become parallel along a narrower portion 115, and meet second edge 118 with a bevel. In use the head of the patient is placed adjacent the first edge 121.

Top plate 113 further has two pairs of elongated handle slots 119,120 extending from the top face 122 through to the bottom face 123, one slot generally adjacent each side edge 114,116, respectively, for carrying. Slots 119,120 are positioned and dimensioned to overlap base plate handle slots 107,108 and together to form two pairs of device handle slots 91,92. In an alternative embodiment, there is one pair of slots adjacent each side edge. In addition, bottom face 123 has a strap slot 124 therein, extending across the narrower portion 115 from side edge 114 to side edge 116 and generally perpendicular thereto. Strap slot 124 is dimensioned to permit a strap to slide therein, an exemplary depth being 0.25 in. When top plate 113 is positioned atop base plate 100, its bottom face 123 adjacent the base plate's top face 111, strap slot 124 and the base plate's top face 111 form a generally rectanglular aperture 125 (see FIG. 1) through which a strap 11, which may comprise a closure such as a hook-and-loop-type fastener, can be placed for securing an area of the patient beneath the lumbar region to the device 10.

In a preferred embodiment, top plate 113 has a length 230 of 39.25 in., a width 231 along wider portion 105 of 16.5 in., a width 232 along narrower portion 103 of 11.75 in., a depth 233 of 0.5 in., and a length along the wider portion 233 of 27.25 in. When top plat 113 is positioned atop base plate 100, the device 10 has a depth 203 of 0.74 in.

Top plate 113 additionally has a generally cylindrical hole 126 extending through from the top face 122 through to the bottom face 123. Hole 126 is positioned with its center within the wider portion 117, with a portion thereof extending into the central section where the side edges 114,116 are angling inward, but does not extend into the narrower portion 115. In a preferred embodiment the center of hole 126 is approximately 16.5 in. from the second edge 118 and has a diameter of approximately 4.8 in.

Surrounding hole 126 and communicating therewith is an annular depression 127. In a preferred embodiment annular depression 127 is 0.25 in. deep and 0.7 in. wide, thereby having an outer diameter of approximately 5.5 in. Extending radially from hole 126 to side edges 114,116 and generally perpendicular thereto are two elongated slots 128,129. In a preferred embodiment, slots 128,129 are approximately 0.5 in. wide and 0.4 in. deep.

Figure 9A:
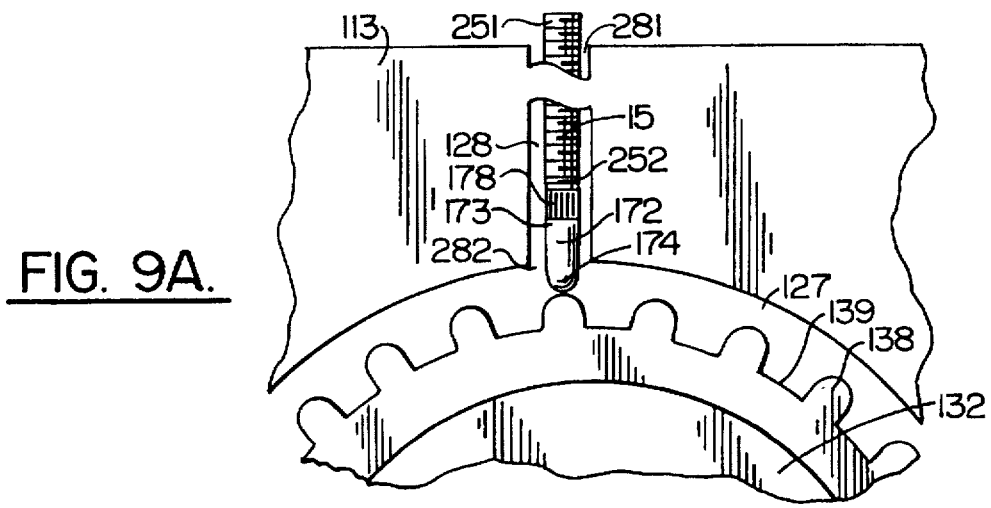
FIG. 9A illustrates the gear/marshmallow spring mechanism in the first position.

Within each of slots 128,129 is positioned a biasing mechanism, the operation of which is discussed in the following. A clicker 400 is positioned within each of the slots 128,129, and will be discussed for slot 128 as being identical with that in slot 129 (see FIGS. 9A and 9B). Clicker 400 is a generally bullet-shaped element having a generally flat first end 173 facing the open first end 281 of the slot 128 and a second end 174 adjacent the open second end 282 of the slot 128, which in turn is adjacent the annular depression 127. Positioned within slot 128 and extending beyong the slot's first end 281 is set screw 15, which is threadable thereinto and adjustable via its first end 251. Between the set screw's second end 252 and the clicker's first end 173 is sandwiched marshmallow spring 178. The set screw 15, clicker 400, and marshmallow spring 178 are relatively dimensioned so that pressure upon the clicker 400 compresses the marshmallow spring 178, which permits the clicker 400 to move into the slot 128 (FIG. 9A), and relaxation of pressure upon the clicker 400 permits its second end 174 to protrude from the slot's second end 282 and into the aperture 127 (FIG. 9B). Set screw 15 is adjustable to permit an adjustment of the extent to which clicker 400 can protrude into the annular aperture 127.

Additionally, the top plate's top face 122 has two threaded screw holes 130,131 therein, positioned symmetrically about the center line and within the wider portion 117, between the hole 126 and the first edge 121. The use for these screw holes 130,131 will be described in the following.

Lumbar support device 10 additionally comprises a generally cylindrical gear 132 (FIGS. 4 and 5) that has a central hole 133 extending therethrough from a top face 134 to a bottom face 135. Gear 132 comprises a narrower cylindrical top portion 136 dimensioned to rotatably fit within the top plate's hole 126 and a wider toothed bottom portion 137 dimensioned to rotatably fit within the top plate's annular slot 127. Gear 132 thus is rotatable with respect to the top plate 113. The teeth 138 situated around the outer edge of the bottom portion 137 are preferably rounded.

In the preferred embodiment with dimensions as given above, top portion 136 has a diameter 310 of approximately 4.75 in. and a depth 311 of 0.25 in., and bottom portion 137 has a diameter 312 of approximately 5.5 in. and a depth 313 of 0.25 in. Hole 133 has a diameter 314 of approximately 0.5 in., and the teeth 138 each have a width 315 of approximately 0.2 in. and are separated by a valley 139 having a width 316 of approximately 0.2 in.

The gear teeth 138 are dimensioned and positioned for engagement with the spring-and-clicker 178/400 biasing mechanism. Specifically, when a tooth 138 is positioned adjacent the slot's second end 282, comprising a first position (FIG. 9A), the clicker 400 is pushed into the slot 128; when a valley 139 is positioned adjacent the slot's second end 282, comprising a second position (FIG. 9B), the clicker 400 is released at least partially thereinto by the decompression of the spring 178, thereby biasing the system into the second position. The rounded edges of the teeth 138 and the rounded second end 174 of the clicker 400 facilitate a rotation of the gear 132 and a movement between the second and the first positions, thereby permitting a movement between successive valleys 139. The clicker 400 is so named because of the audible clicking sound emitted when the clicker 400 moves between the second position and the first position and hits the gear 132. This provides an indicator mechanism, alerting the user that the gear 132 has moved between two sequential indexing positions.

Figure 6:
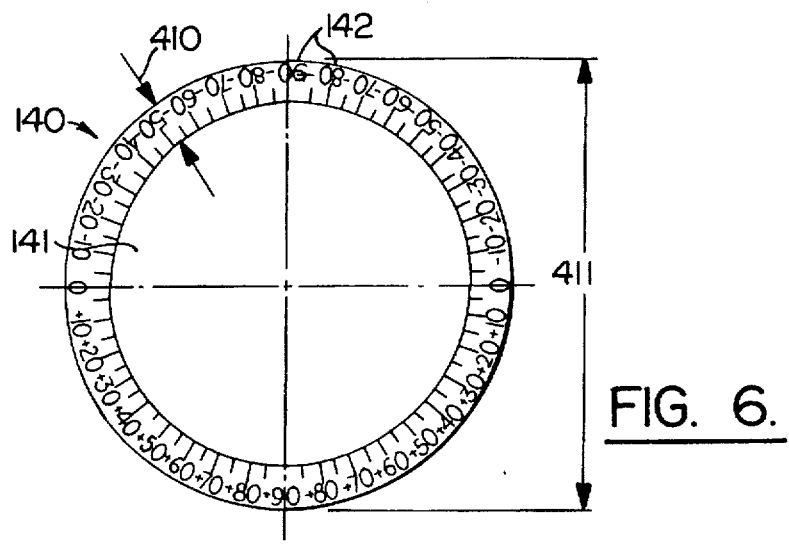
FIG. 6 is a top plan view of the angle indicator.
Figure 7:
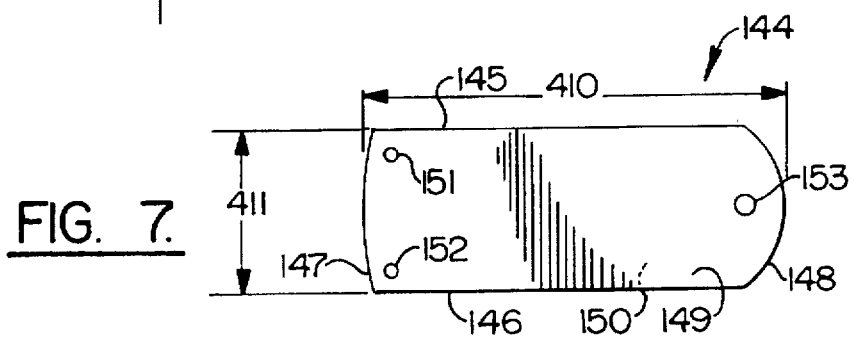
FIG. 7 is a top plan view of the body carriage base.
Figure 8:
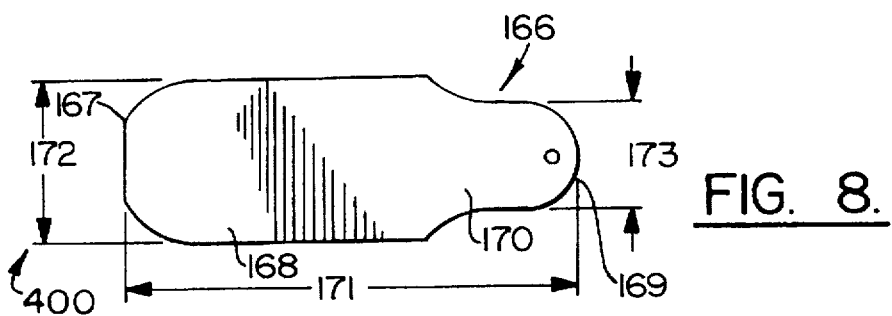
FIG. 8 is a top plan view of the body carriage.

Affixed to the top plate's top face 122 in surrounding relation to hole 126 is generally annular angle indicator 140, having indicia 142 on its top face 141 indicative of angular position therearound. An exemplary angle indicator 140 has angle indicia 142 extending in quadrants of plus and minus 90 degrees, as shown in FIG. 6. In a preferred embodiment the annular width 410 is approximately 1 in., and the outer diameter 411 is 11.5 in. Also in a preferred embodiment the angle indicator 140 comprises a plastic material 1/16 in. thick.

Lumbar support device 10 further comprises a generally flat body carriage base 144 (FIG. 7) having two generally opposed side edges 145,146. A first outwardly curving edge 147 and a second outwardly curving edge 148 each meet side edges 145,146. In a preferred embodiment, body carriage base 144 has a length 410 less than the length 133 of the top plate's wider portion 117 and a width 411 less than the width 131 of the top plate's wider portion 117. The width 411 is further sufficiently small that, when the body carriage base 144 is placed atop the top plate 113 with its long axis generally aligned with the top plate's long axis comprising a first position of the device 10, the body carriage base 144 does not obscure the device's handle slots 91,92 (see FIG. 1). Exemplary dimensions of base 144 are: length 410, 25 in.; width 411, 12 in.; and depth 412, 0.5 in.

Extending through body carriage base 144 from top face 149 through to bottom face 150 are two threaded screw holes 151,152, which are positioned generally in the corners formed by the side edges 145,146 and the first edge 147. Screw holes 151,152 are further positioned to be alignable with top face screw holes 130,131, respectively, when the device 10 is in the first position. Screw holes 130,131,151, 152 are provided so that, during travel or storage, device 10 is lockable in the first position with the use of two locking screws 12 inserted thereinto (see FIG. 1).

Also extending through body carriage base 144 from top face 149 through to bottom face 150 is gear hole 153, which is positioned generally along the center line and adjacent the second edge 148. Gear hole 153 is further positioned to be alignable with top face hole 126 and gear hole 133. The alignment of these three holes 153,126,133 forms a pivot point 95 for the device 10, as will be seen in the following.

Affixed atop the body carriage base 144 are two base spacers 156 (FIG. 1). Spacers 156 are elongated members having a generally flat top surface 157 and three downwardly depending protrusions along the bottom surface 158. First and second protrusions 159,160 are positioned at the ends of the spacers 156; third protrusion 161 is positioned generally centrally between the first and the second protrusions 159,160. Spacers 156 are affixed to the body carriage base's top face 149 with their long axes generally parallel to and symmetrically situated about the center line thereof. When thus affixed, the protrusions 159,160,161 form two apertures 162,163, through which straps 13 are inserted during use to restrain the patient's trunk thereto.

Spacers 156 should preferably have a length 164 less than that 410 of the body carriage base 144. In a preferred embodiment, the spacers 156 are approximately 12.5 in. long, 1 in. wide, and 1 in. high, with the distance between the protrusions 159,160 and 160,161, and hence the length of the apertures 162,163, being 3 in.

Affixed atop the spacers 156 is body carriage 166 (FIG. 8), which preferably has an upward curvature about the center line and is thus adapted for receiving the side of the patient's trunk, including the shoulder. Body carriage 166 is generally paddle-shaped, with a rounded first end 167 adjacent a wider portion 168 and a rounded second end 169 adjacent a narrower portion 170. Body carriage 166 should be shaped so that, when affixed to the spacers 156, and thereby to the body carriage base 144, screw holes 130,131 are not obscured. This is partially accomplished by the upward curvature of the body carriage 166, and is further accomplished by the roundedness of the corners adjacent the first end 167.

Body carriage 166, spacers 156, and body carriage base 144 are affixed together in any of a number of ways known in the art. In a particular embodiment, six nylon screws 14 are inserted through the three elements 166,156,144, three along each of the spacers 156 (see FIG. 1). The body-supporting unit formed by these three elements 166,156,144 is pivotably affixed at pivot point 95 to the base unit formed by the top plate 113 and base plate 100. As the body-supporting unit is also affixed to the gear 132, a movement thereof also moves the gear 132. Thus the body-supporting unit is movable from a first position (FIG. 1) with the center lines generally aligned to a second position (FIG. 10) with the center lines at an angle away from parallel. During this movement, the clicker 400 provides an audible indication each time a gear tooth 138 is passed, and the angle of the body-supporting unit can be read off from the angle indicator 140, thereby providing a repeatable position.

In a preferred embodiment, body carriage 166 is formed of clear acrylic and has a length 171 of 19.5 in., a width 172 of the wider portion 168 of 6.75 in., a width 173 of the narrower portion 170 of 5.5 in., and a depth 174 of 0.4 in.

The method of utilizing the apparatus 10 to perform imaging of the lumbar region of a patient comprises the step of positioning the patient on his side upon the body carriage 166 so that his shoulder and upper trunk are cradled thereby. Next upper straps 13, which have been inserted through apertures 162,163 and around the bottom of the base carriage 166, are affixed around the patient's back and downwardly facing arm, and lower strap 11, which has been inserted through aperture 125, is affixed around the patient's upper thighs.

Once the apparatus 10 and patient have been inserted into the imaging system, the patient is instructed to bend at the waist in predetermined increments, from the first position (FIG. 1) to a second position (FIG. 10), and preferably to a series of positions, the angular measurements of which are readable from the angle indicator 140 using, for example, the second edge 148 of the body carriage base 144 as a pointer. A series of images are then taken at each position, which then can be used to provide an indication of any joint disorder.

It may be appreciated by one skilled in the art that additional embodiments may be contemplated, including similarly conceived devices for indexing other bodily joints and for alternative imaging technologies.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A support and indexing apparatus for magnetic resonance imaging a lumbar region of a patient comprising:

a base adapted for insertion into a magnetic resonance imaging apparatus;

a support structure rotatably affixed at a pivot point atop the base, the support structure adapted for receiving a side of a trunk of the patient, the pivot point positioned to permit flexion and extension of the lumbar region;

biasing means for preferentially positioning the support structure in one of a sequential series of rotational positions relative to the base, the support structure rotatable by exerting sufficient force about the lumbar region around the pivot point to overcome the biasing means;

and index means for providing an angular measurement of the rotational position;

wherein the support structure comprises a generally flat body carriage base pivotably affixed atop the base; and a body carriage having an upward curvature about a center line for cradling the trunk side, the body carriage affixed atop the body carriage base and positioned to support a waist of the patient in vertical alignment with the pivot point;

and wherein the base has a generally cylindrical hole in a top portion thereof, a center of the hole positioned generally at the pivot point, and a slot in the base top portion extending radially outward from the hole;

the support structure comprises a gear affixed to a bottom face of the body carriage base, the gear positioned and dimensioned to closely rotate within the base hole;

the biasing means comprises a clicker positioned within the slot, the clicker movable between a first position substantially entirely within the slot and a second position wherein at least a portion of the clicker protrudes from an inner end of the slot, the clicker biased to the second position; and a gear tooth adjacent the slot retains the clicker within the slot and a gear valley adjacent the slot permits the clicker to move to the second position.

2. The support and indexing apparatus recited in claim 1, further comprising indicator means for communicating a rotation of the support structure relative to the base between a one and an adjacent one of the sequential locations.

3. The support and indexing apparatus recited in claim 1, further comprising spring means positioned within the slot between an outer end of the slot and the clicker.

4. The support and indexing apparatus recited in claim 3, wherein the spring means comprises a marshmallow spring.

5. The support and indexing apparatus recited in claim 3, further comprising means for adjusting a position of the spring means within the slot positioned adjacent the slot outer end.

* * * * *